United States Patent
Kenney et al.

(10) Patent No.: US 6,645,928 B1
(45) Date of Patent: *Nov. 11, 2003

(54) HYDROPHOBIC LIQUID PHOTOBLEACHES

(75) Inventors: Malcolm Edward Kenney, Cleveland Heights, OH (US); Ying-Syi Li, Highland Heights, OH (US); Gongzhen Cheng, Hubei (CN); Rafael Ortiz, Milford, OH (US); David Johnathan Kitko, Cincinnati, OH (US); Michael Eugene Burns, Hamilton, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/936,059

(22) PCT Filed: Mar. 1, 2000

(86) PCT No.: PCT/US00/05256

§ 371 (c)(1),
(2), (4) Date: Feb. 11, 2002

(87) PCT Pub. No.: WO00/52121

PCT Pub. Date: Sep. 8, 2000

Related U.S. Application Data

(60) Provisional application No. 60/123,050, filed on Mar. 5, 1999.

(51) Int. Cl.[7] .............................. C11D 3/20; C11D 3/26

(52) U.S. Cl. ................ 510/394; 510/311; 510/370; 510/376; 510/499; 540/122; 540/123; 540/128; 8/137

(58) Field of Search .......................... 510/311, 376, 510/370, 499, 394; 540/122, 123, 128; 8/137

(56) References Cited

U.S. PATENT DOCUMENTS

| | | | | |
|---|---|---|---|---|
| 4,256,597 A | * | 3/1981 | Sakkab ...................... 252/99 |
| 4,400,173 A | * | 8/1983 | Beavan ....................... 8/107 |
| 5,358,940 A | * | 10/1994 | Capraro et al. ............... 514/63 |
| 5,817,614 A | * | 10/1998 | Miracle et al. .............. 510/376 |
| 5,916,481 A | * | 6/1999 | Willey ................... 252/186.21 |
| 5,958,858 A | * | 9/1999 | Bettiol et al. ............... 510/351 |
| 6,197,070 B1 | * | 3/2001 | Horner et al. .................. 8/137 |
| 6,218,351 B1 | * | 4/2001 | Busch et al. ................ 510/311 |
| 6,339,055 B1 | * | 1/2002 | Brooker et al. ............. 510/301 |

FOREIGN PATENT DOCUMENTS

| | | | |
|---|---|---|---|
| EP | 899325 | * | 3/1999 |
| WO | WO 97/05203 | * | 2/1997 |
| WO | WO 98/32826 | * | 7/1998 |

* cited by examiner

*Primary Examiner*—Gregory Delcotto
(74) *Attorney, Agent, or Firm*—Fay, Sharpe, Fagan, Minnich & McKee, LLP

(57) ABSTRACT

Nonionic, hydrophobic photobleach compounds, especially those based on Si(IV) phthalocyanines, which are liquid at ambient temperatures and their use in a variety of consumer product compositions.

9 Claims, No Drawings

HYDROPHOBIC LIQUID PHOTOBLEACHES

This application claims priority under 35 USC 119(e) to U.S. Provisional Application No. 60/123,050, filed Mar. 5, 1999.

FIELD OF THE INVENTION

The present invention is in the field of photobleaches, especially photobleaches which are hydrophobically substituted metal or metalloid phthalocyanine compounds useful for treating fabrics, e.g., in consumer products such as laundry detergents.

BACKGROUND OF THE INVENTION

Historically, photobleaches in consumer products have been ionic, usually as a result of sulfonation. Salt forms are typically used. This improves water-solubility and decreases interaction with common anionic surfactants used in detergents, but increases melting-point of the photobleach relative to a non-charged or non-salt material. Making a photobleach hydrophilic and giving it anionic charge also reduces its ability to partition into, and, upon exposure to light, to bleach oily soils and stains.

Recently, certain non-charged (nonionic) photobleaches have been developed. These include non-charged photobleaches among those disclosed in WO 98/32832 A, WO 98/32829 A, WO 98/32828 A, WO 98/32827 A, WO 98/32826 A, WO 98/32825 A, and WO 98/32824 A all published Jul. 30, 1998; and WO 97/05203 A and WO 97/05202 published Feb. 13, 1997. These materials can be quite hydrophobic and are useful in laundry detergents. They have an improved ability to treat oily soils.

While nonionic photobleaches generally have lower melting-points than ionic photobleaches, it is believed that the nonionic photobleaches thusfar disclosed, at least in pure form, are solids at ambient temperature. Recent advances in such photobleaches indeed appear to have focused on improving the photophysics without sufficient regard to certain design characteristics, including melting-point, which may be very important to the formulator of consumer products.

Chromophores such as phthalocyanines are typically of relatively high symmetry, thus nonionic photobleaches comprising such chromophores tend to have higher melting-points than many common nonionic organic compounds.

Thus, despite the recent advances, there remains a need for further improvements in photobleaches for use in consumer products. Specifically, there is an ongoing need for photobleaches which are more hydrophobic, more useful for treating synthetic or lipid-soiled fabrics, and are capable of being uniformly dispersed without milling the crystals. Uniform dispersion is very important to avoid a patchy effect in photobleaching of fabrics. Yet, in particular, there is no known consumer product composition having a hydrophobic, liquid photobleaching compound. Such a photobleach compound would offer new possibilities to the formulator of consumer products, could be deposited more uniformly, and would offer economic advantages such as low energy input and the ability to avoid solvents when compounding or formulating the photobleach.

It is accordingly an object of the present invention to provide further improvements in photobleach compounds, especially with respect to types wherein the photobleach is hydrophobic. Indeed it is an object herein to provide novel photobleaches which are hydrophobic nonionic liquids at ambient temperature; and to provide all manner of novel consumer product compositions comprising such compounds.

These and other objects are accomplished herein, as will be seen from the following disclosure.

BACKGROUND ART

See for example U.S. Pat. No. 5,872,248; U.S. Pat. No. 5,484,778; U.S. Pat. No. 5,763,602; Derwent 93-032275; EP-284,370 A; EP-296,876; EP-366,440; EP-484,027 A; EP 538,228 A; EP-596,184; GB 2,260,996; GB 2,279,657; GB 2,313,122; JP 3285998 (See Derwent 92-038692); JP 51/39044; JP 52/55339; JP 60/48047; JP 61/57536; JP 7292398 A (see Derwent 96-017535); KR 97-61275; KR 9102515 (see Derwent 92-321309); U.S. Pat. No. 3,860,484; U.S. Pat. No. 4,166,718; U.S. Pat. No. 4,209,417; U.S. Pat. No. 4,304,719; U.S. Pat. No. 4,368,053; U.S. Pat. No. 4,800,188; U.S. Pat. No. 4,806,514; U.S. Pat. No. 4,911,919; U.S. Pat. No. 5,135,717; U.S. Pat. No. 5,280,183; U.S. Pat. No. 5,346,670; U.S. Pat. No. 5,437,929; U.S. Pat. No. 5,482,514; U.S. Pat. No. 5,484,778; U.S. Pat. No. 5,561,106; U.S. Pat. No. 5,585,483; U.S. Pat. No. 5,665,689; U.S. Pat. No. 5,665,875; U.S. Pat. No. 5,679,661; U.S. Pat. No. 5,733,560; U.S. Pat. No. 5,824,800; WO 91/18006; WO 91/18007; WO 92/01753; WO 92/01753; WO 94/22960; WO 95/06688; WO 95/24267; WO 95/31526; WO96/29367; WO 97/05202; WO 97/05202; WO 97/05203; WO 97/10811; WO 98/14521; WO 98/25455; WO 98/32827; WO 98/32832; and WO 98/44052.

See also U.S. Pat. No. 3,094,536, Jun. 18, 1963; U.S. Pat. No. 3,927,967, Dec. 23, 1975; U.S. Pat. No. 4,033,718, Jul. 5, 1977; U.S. Pat. No. 4,240,920, Dec. 23, 1980; U.S. Pat. No. 4,255,273, Mar. 10, 1981; U.S. Pat. No. 4,256,597, Mar. 17, 1981; U.S. Pat. No. 4,318,883, Mar. 9, 1982; U.S. Pat. No. 4,497,741, Feb. 5, 1985; U.S. Pat. No. 4,648,992, Mar. 10, 1987; and U.K. Pat. Appl. 1,372,035 published Oct. 30, 1974; U.K. Pat. Appl. 1,408,144 published Oct. 1, 1975; U.K. Pat. Appl. 2,159,516 published Dec. 4, 1985; E.P. 285,965 A2; E.P. 381,211 A2 published Aug. 8, 1990; E.P. 484,027 A1 published May 6, 1992; and Japanese Kokai 06-73397 Derwent Abst. No. (94-128933) published Mar. 15, 1994.

In addition to the above, other references describe the synthesis, preparation and properties of phthalocyanines and naphthalocyanines; see *Phthalocyanines: Properties and Applications*, Leznoff, C. C. and Lever A. B. P. (Eds), VCH, 1989; *Infrared Absorbing Dyes*, Matsuoka, M. (Ed), Plenum, 1990; *Inorg. Chem.*, Lowery, M. J. et al., 4, pg. 128, (1965); *Inorg. Chem.* Joyner R. D. et al., 1, pg. 236, (1962); *Inorg. Chem.*, Kroenke, W. E. et al., 3, 696, 1964; *Inorg. Chem.* Esposito, J. N. et al., 5, pg.1979, (1966); *J. Am. Chem. Soc.* Wheeler, B. L. et al., 106, pg. 7404, (1984); *Inorg. Chem.* Ford, W. E, et al., 31, pg. 3371, (1992); *Material Science*, Witkiewicz, Z. et al., 11, pg. 39, (1978); *J. Chem. Soc.* Perkin Trans. I, Cook, M. J., et al., pg. 2453, (1988); *J. Chin. Chem. Soc.*, 40, pg. 141, (1993); *J. Inorg. Nucl. Chem.*, 28, pg. 899, (1966); *Polymer Preps*, 25, pg. 234, (1986); *Chem. Lett.*, 2137, (1990); *J. Med. Chem.*, 37, pg. 415, (1994).

SUMMARY OF THE INVENTION

The present invention encompasses improvements in a nonionic photobleach compound for consumer product application having (A) a metal or metalloid, preferably selected from Ga, Ge, Sn, Si and Al; (B) a chromophore, preferably selected from phthalocyanine and naphthalocyanine (wherein this encompasses both substituted and unsubstituted phthalocyanines and naphthalocyanines); and (C) one or two bonded ligands, preferably occupying axial positions. The improvement comprises at least one, covalently attached, hydrophobic, strongly crystallinity-disrupting or symmetry-lowering substituent in said chromophore, said bonded ligand in axial position, or in combinations thereof; whereby said nonionic photobleach compound has crystal packing substantially disrupted to the extent that it is a liquid at ambient temperature.

"Ambient temperature" is typically about 20° C., but can vary from country to country and from season to season. As defined herein, however, "liquid at ambient temperature" means specifically that the present photobleach compounds are liquid at a temperature below about 35° C., including that they are liquid at at least one temperature in the range from 0° C. to about 35° C., more preferably, that they are liquid at all temperatures in the range from about 15° C. to about 25° C. Moreover with respect to melting-points of photobleaches herein, such melting-points are generally determined on samples of substantially pure photobleach materials, for example those which are substantially free from consumer product adjuncts or starting-materials of the synthesis. "Substantially free" means that such adjuncts or starting-materials are removed to the extent practically possible. Likewise the term "substantially pure" as applied to the photobleaches herein means that the photobleach compound, for purposes of characterization, is accompanied by no adjuncts, starting-materials or impurities to the extent that such adjuncts, impurities, or starting-materials may be practically removed by normal purification techniques, such as chromatography, low-temperature crystallization, or the like.

In alternative terms, the invention encompasses a nonionic photobleach compound for consumer product application, preferably characterized by (A) a metal or metalloid selected from Ga, Ge, Sn, Si and Al; (B) a chromophore selected from phthalocyanine and naphthalocyanine; and (C) one or two bonded ligands, occupying axial positions; wherein said nonionic photobleach compound comprises at least one, covalently attached, substituent in said chromophore, said bonded ligand in axial position, or combinations thereof; wherein said covalently attached substituent is selected from the group consisting of hydrophobic, strongly crystallinity-disrupting or symmetry-lowering substituents; and wherein said nonionic photobleach compound is a liquid at ambient temperature.

The present nonionic photobleach compounds are useful in consumer products, as will be seen from the following disclosure.

The invention has many other ramifications and embodiments, and numerous advantages, as will also be seen from the disclosure. All percentages and proportions herein are by weight unless otherwise indicated. The units of parts per million or "ppm" wherein 1 ppm=1 milligram per liter=0.0001% by weight may alternatively be used herein from time to time, especially for content of photobleach compound in a composition of the invention.

All documents cited herein are incorporated by reference in their entirety.

DETAILED DESCRIPTION OF THE INVENTION

Preferred Embodiments

As noted in summary, the present photobleach compounds comprise covalently attached substituents which make the compounds very hydrophobic, substantially lower the symmetry, and reduce the melting-point.

In one preferred embodiment, said covalently attached substituent is attached to said ligands occupying axial positions.

In another preferred embodiment, said covalently attached substituent is attached to said chromophore.

It is especially suitable for various purposes, including convenience of synthesis and lower overall cost, to have the covalently attached substituent attached to the ligands occupying axial positions.

In a preferred embodiment, said covalently attached substituent comprises at least one hydrocarbyl moiety comprising about 10 or more carbon atoms; preferably said covalently attached substituent comprises at least one branch-point.

A "branch-point" of a covalently attached substituent herein is any stereochemical departure from a n-hydrocarbon structure which will result in an increased inefficiency of crystal packing or of liquid crystal packing of a pure hydrocarbon corresponding to the substructure having the branch-point.

Branch-points are non-limitingly illustrated by iso- and tert- hydrocarbon structures. For example, the following substructures contain branch-points:

In general, branch-points are not limited to carbon and hydrogen. For example, an amino nitrogen atom can act as a branch-point.

More preferably still, said axial ligand comprises at least two of said substituents and additionally comprises at least one covalently attached substituent comprising at least one hydrocarbyl moiety having about 12 or more carbon atoms. This creates a nonionic photobleach compound whose properties, especially with respect to crystal packing, are very heavily influenced by the ligand, counterbalancing the high symmetry and inclination to pack in a crystal lattice which is characteristic of the chromophore.

More generally, the present photobleaches include those having at least one of said substituents, wherein the substituents can be located on the chromophore or on the axial ligands, e.g., any of S'–S'''' in the nonlimiting illustrative structure below wherein the chromophore is based on a phthalocyanine.

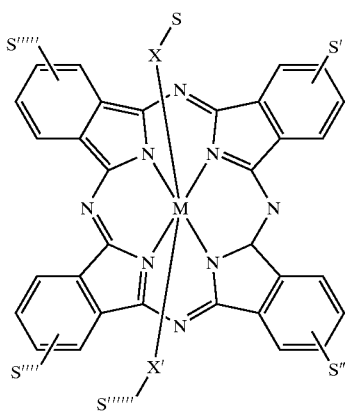

Moreover, there can, in general, be two or more substituents meeting the present requirements on any of the rings of the chromophore, or anywhere in the molecule.

In highly preferred hydrophobic photobleach compounds herein, the metal or metalloid is Si(IV). While it is possible to substitute the chromophore rather than the axial ligands, in preferred embodiments, the photobleach compound has as the chromophore a phthalocyanine, preferably one wherein the phthalocyanine is free from any of said substituents. All the substituents meeting the present needs are thus located on the axial ligands.

A preferred nonionic photobleach compound herein has the formula: $Si(IV)(Pc)L_2$ wherein Pc=phthalocyanine and L represents said axial ligands; and wherein each L can vary independently and is selected from the group consisting of: —$OSi(R^1)(OR^2)_2$ wherein $R^1$ is a hydrocarbyl moiety having 12 or more carbon atoms and $R^2$ is a branched hydrocarbyl moiety having 10 or more carbon atoms. One such nonionic photobleach compound has the formula:

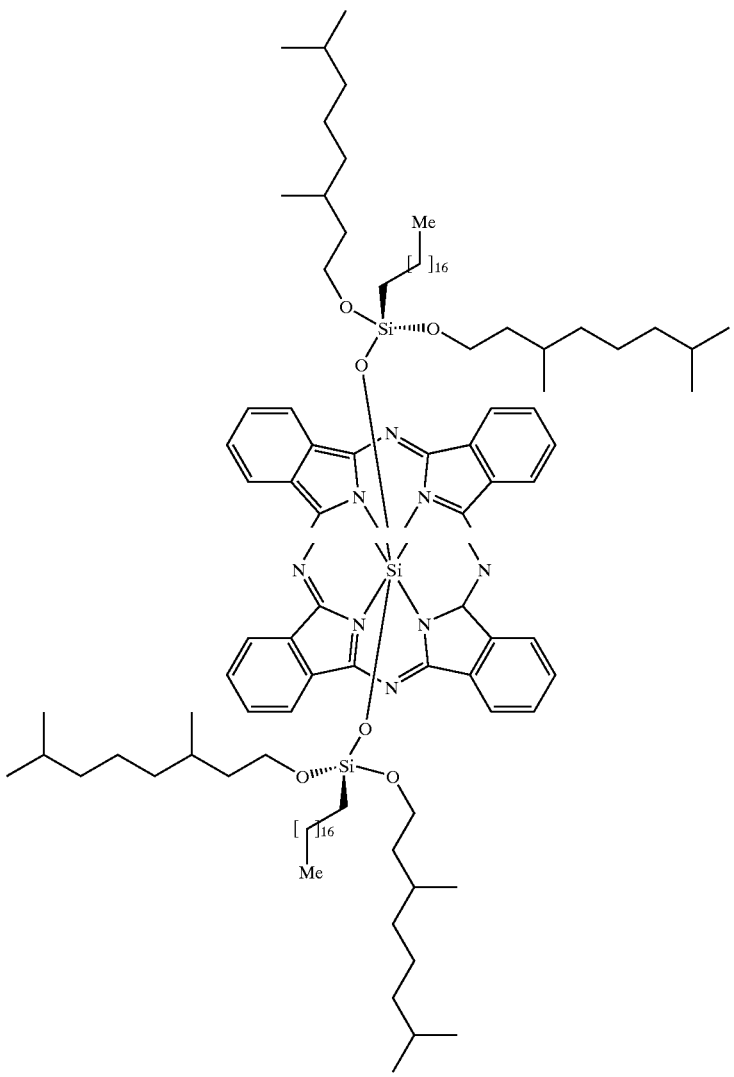

The present invention also includes all forms of consumer product composition comprising the photobleach compounds of the invent ion. Such consumer product compositions generally comprise the photobleach compound and at least one adjunct material which can vary widely, including, for example, propellants (for an aerosol delivery), organic solvents including fluorocarbons, adjuncts of detergents or of dry-cleaning products, or adjuncts of fabric conditioners. All that is generally required is that the novel photobleach compound be present. Typically, a consumer product composition herein comprises at least about 0.001 ppm of the nonionic photobleach compound of the invention.

While the invention can be used to treat fabrics or other surfaces encountered by the consumer of any kind, the present photobleach compounds are especially suitable for treating hydrophobic textile fabrics, including those having some yellowing, even when clean. The treatment can use any suitable method, whether aqueous or non-aqueous. For example, fabrics can be treated in a dry-cleaning operation using any known dry-cleaning medium, with the present compounds. One preferred treatment is for so-called "dingy" fabrics, which are often yellowed by the presence of complex lipid soils.

Thus, the invention encompasses a method of cleaning a dingy fabric comprising a step of treating the dingy fabric with a consumer product composition comprising a hydrophobic nonionic photobleach compound wherein said compound in substantially pure form is a liquid at ambient temperature; preferably the photobleach is a preferred compound of the invention such as a Si(IV) phthalocyanine bearing axial substituents of the type non-limitingly illustrated herein. Such a method extends to a variety of consumer product compositions, such as those in which the consumer product is a member selected from the group consisting of: (i) laundry or dry-cleaning pre-treaters; (ii) laundry detergents; (iii) fabric softeners; and (iv) aerosol or spray-based fabric treatments other than (i)–(iii).

The present invention also includes a process for providing intermediate compositions of formulated photobleaches for use in consumer products, or for improving ease of formation thereof, said process comprising the steps of: (a) providing a nonionic photobleach compound which in substantially pure form is liquid at ambient temperature; and (b) mixing said photobleach compound with one or more adjuncts, thereby forming an intimate mixture of said photobleach in said adjunct or adjuncts; whereby, by virtue of the liquid form of said nonionic photobleach compound, there is no need for high-energy mixing, milling, or use of solvents to accomplish good mixture.

Photobleach Compounds

As formulated in consumer products, in addition to the adjuncts required for making or delivering the full benefit of such compositions, the present invention requires that the inventive compositions comprise an effective amount of a particularly defined and selected photobleach compound.

The preferred photobleach compounds have no charged moieties, i.e., they are "nonionic", and they are metal or metalloid phthalocyanines comprising one or two chemically bound ligands occupying axial positions.

The present compositions thus comprise a hydrophobic photobleach compound as an essential component. The term "hydrophobic" is used in conjunction with the photobleaches to distinguish the photobleaches herein from "hydrophilic" photobleaches which are well-known in the art: these hydrophilic photobleaches generally comprise at least one anionically charged group, such as a sulfonate group, which confers water-solubility.

The present photobleaches are generally hydrophobic to the extent that when placed in a two-phase mixture of water and common organic solvents such as methylene dichloride, they will preferentially and strongly partition into the organic phase, not the water phase. Hydrophobic photobleach compounds herein are non-charged, or "nonionic".

All highly preferred photobleach compounds of the invention are sufficiently hydrophobic to partition at least partially from a phase which is more hydrophilic than triolein, into triolein.

Chromophore

Photobleaches herein generally comprise a chromophore in the form of a planar or distorted-planar extended cyclic system acting as a polydentate ligand occupying equatorial positions with respect to a metal or metalloid. Together, the chromophore, the metal or metalloid and one or two additional ligands occupying axial positions form a photoactive compound. Preferred chromophores are selected from unsubstituted phthalocyanine and naphthalocyanine (preferably phthalocyanine). Optionally, substituents may be attached to the cyanine provided said photobleach is not thereby rendered substantially soluble in water. Substituents, if present, are noncharged; sulfonate substituents are excluded from all preferred embodiments.

Metal or Metalloid

Photobleaches herein generally comprise a metal or metalloid selected from the group consisting of Si, Al, Ga, Ge and Sn, more preferably Si and Al, more preferably still, Si. The metal or metalloid, shown as "M" in the following structures, is bound to both to the chromophore and to ligands occupying axial positions, marked X or X' in these structures.

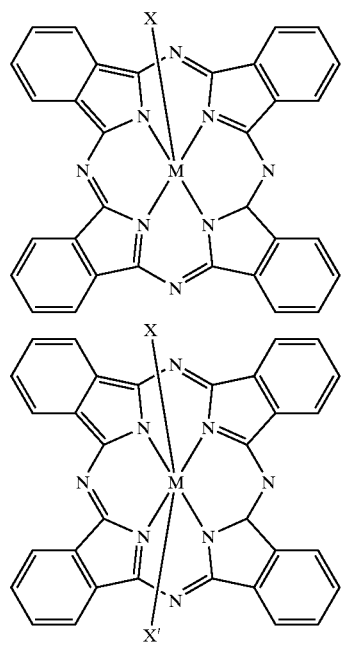

In highly preferred detergent compositions of the invention, the photobleach compound is selected from the group consisting of:

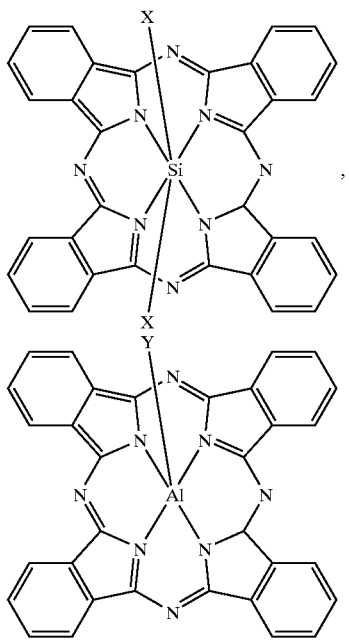

and mixtures thereof wherein X and Y can vary independently and represent axially bonded ligands.

Photobleach Precursor

Photobleaches herein are commonly prepared from a precursor compound. A common precursor is the dihydroxy Si(IV) phthalocyanine of formula:

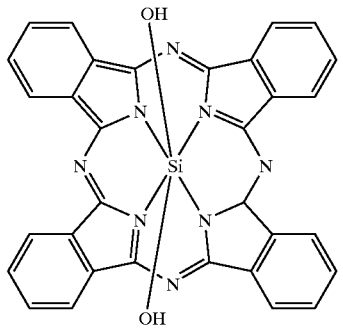

"Ligand", Axial Position, Axial Site Available, "Axial Ligand", "Bonded Ligand"

The term "ligand" herein most generally refers to an organic compound other than phthalocyanine or naphthalocyanine (thus specifically excluding inorganic moieties such as water, —OH, —Cl etc. as in the precursor compound above). The ligand is an organic compound capable of binding axially to a Si, Al, Ga, Ge or Sn (preferably Si(IV)) phthalocyanine moiety. The invention does not exclude Si(IV) phthalocyanines comprising one organic axial ligand and one —OH ligand, but preferably, when the metalloid is Si, the photobleach will have two non-OH organic ligands.

The terms "bonded ligand" or "axial ligand" or "ligand in axial position" herein are used to distinguish ligand which is actually chemically bonded to the metal or metalloid, from any other ligand, e.g., which is simply present in physical admixture with the metal or metalloid compound.

The term "axial" as in "axial position", or "axial ligand", is used herein to indicate a position of bonding with respect to a metal or metalloid. Specifically, in the case of phthalocyanine compounds for example, the phthalocyanine chromophore occupies "equatorial positions" while all non-phthalocyanine ligands occupy "axial positions". In Si(IV) phthalocyanines there are two axial positions, whereas in Al phthalocyanines, there is only one. Thus, a "bonded axial ligand" is by definition a ligand which is not the chromophore, bonded to the metal or metalloid.

On bonding to the photobleach precursor, a ligand molecule may lose a small portion of its mass, for example due to elimination of water or a silanol on reaction with a hydroxyfunctional photobleach precursor. For example when the molecule eliminated is water, the bonded ligand has a molecular weight of 1 less than that of the free or nonbonded ligand.

Photobleach Hue

The photobleaches herein can have any visible hue consistent with the chromophore. Hue preference of laundered fabrics tends to vary from one country or region to another, and can include blue, green or pink hues.

Consumer Product or Detergent Compositions

The present invention encompasses consumer product compositions, including pre-treaters such as stain-sticks or aerosol sprays free from detergent surfactants, as well as laundry detergents for laundering soiled garments or fabrics in dry-cleaning appliances, automatic washing machines or by hand. A "detergent composition" is a composition having any suitable form, such as granules, powders, tablets, liquids, gels, pastes or the like, and comprising an effective amount of at least one detersive surfactant capable of removing soils from soiled clothing and an effective amount of least one non-surfactant detergent adjunct. Other forms of consumer product composition forming part of the invention do not require the detersive surfactant.

Effective Amounts of Components

An "effective amount" of a consumer product ingredient is an amount capable of at least partially improving the appearance thereof by removal, chemical modification, or physical altering of soil.

An "effective amount" of a photobleach compound is any amount of a photobleach compound capable of improving the appearance of a fabric through any photophysical mechanism, be it catalytic or stoichiometric. The improvement may happen in dry-cleaning, washing or laundering stages, or in subsequent stages, such as line drying in the sun.

Typical "effective amounts" of photobleaches can be very low, e.g., parts per billion, more typically a few parts per million up to about 10,000 ppm in a consumer product composition.

"Effective amounts" with respect to detersive surfactants are amounts consistent with exceeding the critical micelle concentration of a single detersive surfactant under the conditions of use, or, when multiple detersive surfactants are used, the in-use concentration of the combination of detersive surfactants is sufficient for forming micelles.

Levels of Photobleach Compound in Consumer Product Compositions

In general, the photobleach compounds herein can be used at any level providing photobleaching. However, low levels are preferred to avoid staining or overhueing. Suitable levels include from about 0.015 ppm to about 0.5%, more preferably from about 0.010% to about 0.050%, more preferably still from about 0.001% to about 0.01% of hydrophobic photobleach compound in a consumer product composition.

Adjuncts

Any adjuncts other than the photobleach compound or detersive surfactant can be useful herein. A "non-surfactant detergent adjunct" is any component suitable for incorporation in a consumer product, e.g., a laundry detergent, provided that this component is other than a detersive surfactant or a photobleach. Such a component can include, for example, solvents, propellants, polymeric carriers or vehicles, builders, chelants, bleach systems, soil release polymers, softeners, perfumes and the like.

Preferred non-surfactant detergent adjuncts include bleach systems, (especially those comprising hydrophobic bleach activators such as nonanoyloxybenzene sulfonate and/or transition metal bleach catalysts such as Mn or Fe complexes of rigid macrocyclic donors and/or organic bleach boosters), enzyme systems (including both bleaching and non-bleaching enzymes), builders (including sodium tripolyphosphate as well as nonphosphate detergency builders), silicone/silica compounded antifoams, end-capped terephthalate-based soil release polymers, optical brighteners, and pro-perfumes.

In addition to adjuncts provided for directly consumer-useful purposes, the present photobleach compounds can be formulated with other optional components, for example external coatings and/or cationic additives, processing aids or the like.

Detersive Surfactants

A "detersive surfactant" is an amphiphilic compound, typically at least partially water-soluble, preferably completely water-soluble, having at least one hydrophobic moiety, called a "tail", typically comprising a linear or branched hydrocarbyl moiety comprising at least six carbon atoms, and at least one hydrophilic moiety, called a "head-group". The head-group may be charged or non-charged. Conmmon detersive surfactants include anionic, cationic, nonionic and zwitterionic types, extensively recited in patents of detergent formulators and other publications.

When the compositions of the invention are detergent compositions, they comprise, in addition to the photobleach compound, a detersive surfactant, suitably at levels of from about 0.1% to about 99.9%, more preferably from about 0.5% to about 50%, typically from about 1% to about 30% by weight of the detergent composition. In general, the detersive surfactant can be selected from the common commercial detersive surfactants sold for laundry detergent use, including especially anionic detersive surfactants, particularly alkylbenzene sulfonates, alkyl sulfates, methyl ester sulfonates, or mixtures thereof; and nonionic detersive surfactants, particularly alkyl alkoxylates, sugar-derived nonionic surfactants such as APG's or glucosamides, or mixtures thereof. Mixtures of anionic and nonionic detersive surfactants at ratios of from about 1:10 to about 10:1 by weight can be especially useful. Any suitable chainlength or carbon content of the hydrophobe of these surfactants can be used, for example from about $C_8$ to about $C_{20}$, more typically from about $C_8$ to about $C_{17}$. Any degree or type of branching in the hydrophobe is acceptable. The alkylbenzene sulfonates are often used at lower carbon content, for example an average of about $C_{10}$ to $C_{12}$. When the surfactant is anionic, most commonly it is used in the sodium salt form, though other forms, for example potassium, can be used for known reasons such as to promote solubility. Any specialty surfactants, for example foam boosters, can be added if desired.

Polymeric Delivery Vehicles

The present photobleach compounds can, if desired, be formulated with a polymer as a delivery vehicle, for example to protect the hydrophobic photobleach herein from detersive surfactants or other adjuncts, or to help improve total amount or uniformity of deposition. Preferred polymeric delivery vehicles include thermoplastic polymers which soften or melt under conditions of use, e.g., those which are liquid or molten at temperatures less than about 95° C., and water-soluble polymers. Which polymer delivery system to use, and how hydrophobic it should be, are highly dependent on the precise type of consumer product. For example, in laundry detergents, polyalkylene glycols and/or mixed poly-alkylene glycols, such as polyethylene glycols, having average molecular weights of from about 150 to about 20,000, preferably between about 600 and about 10,000, more preferably still from about 3,000 to about 6,000, e.g., about 4,000 are very useful. Another group of water-soluble polymers are water-soluble polymers which include N as an amide, including, especially, water-soluble polymers comprising as monomeric units vinylamides such as N-vinylpyrrolidone and N-vinylacetamide as well as vinyl heterocycles such as N-vinylimidazole, N-vinyloxazolidone, N-vinyltriazole, 4-vinylpyridine, and 4-vinylpyridine-N-oxide; or poly-(N-isopropyl acrylarnide). Most preferred water-soluble polymer compounds in this group in accordance with this invention are polyvinylimidazole (PVI), or a copolymer of polyvinylpyrrolidone and polyvinylimidazole (PVPVI), most preferably polyvinylpyrrolidone (PVP). Preferably, these highly preferred amidofunctional water-soluble polymers have an average molecular weight of from 20,000 to 60,000. Also suitable herein as polymeric delivery vehicles are mixtures of two or more of any of the foregoing water-soluble polymers. Levels of such polymers in compositions herein can vary widely, but include, when present, at least about 0.001% to about 99.99%, more preferably from about 0.01% to about 25%, more preferably and typically from about 0.05% to about 0.5% of polymer.

Optional Components—Coatings

The present compositions can moreover include variants which comprise an external coating or other encapsulation means for the photobleach compound.

For example, when formulating the photobleach in an aqueous liquid detergent composition, it may be desirable to further coat or protect particles comprising the photobleach with a coating or hardening material such as a microcrystalline wax. Such coating or protection can help ensure better integrity of the photobleach delivery system particles on storage in the liquid detergent composition. Of course, such coatings can be used also when the photobleach delivery system is intended to be incorporated in granules, powders, pastes or tablet forms of the detergent composition.

Levels of such coatings in compositions herein can vary widely, but include, when present, at least about 0.001% to about 99.99%, more preferably from about 0.01% to about 25%, more preferably and typically from about 0.05% to about 0.5% of coating or encapsulating material.

Optional Components to be Formulated With Photobleach Compound

The present photobleaches can be coformulated with any adjunct materials other than cleaning actives. This includes cationic polymers such as cationic starches, polyethyleneimine polymers or copolymers, quaternary ammonium salts of the type used in fabric conditioners or through-the-wash softeners, or the like. Such cationic additives may further improve deposition of the photobleach on fabrics in certain detergent compositions, especially those wherein the detersive surfactant component is to a large extent nonionic rather than anionic.

Levels of optional components in compositions herein can vary widely, but include, when present, at least about 0.001% to about 90%, more preferably from about 0.01% to about 25%, more preferably and typically from about 0.05% to about 0.5% of the optional component or adjunct.

Any other optional component consistent with the spirit and scope of the invention may be added to the photobleach, provided that it does not result in a consumer product composition which provides no photobleaching.

Non-Surfactant Detergent Adjunct

Detergent compositions herein suitably comprise at least one nonsurfactant detergent adjunct. Preferably said nonsurfactant detergent adjunct comprises one or more members selected from the group consisting of: bleaching enzymes; non-bleaching enzymes; transition metal bleach catalysts; organic bleach boosters; bleach activators; oxygen bleach sources; preformed peracids; soil release agents; builders; chelants; conventional water-soluble sulfonated photobleaches; and mixtures of any of these adjuncts. Suitable levels of nonsurfactant detergent adjuncts in the inventive compositions can vary widely. For example, in detergent compositions of the invention, the composition suitably comprises from about 0.0001% to about 99%, more preferably from about 1% to about 90%, typically from about 20% to about 85% by weight of the detergent composition of at least one non-surfactant detergent adjunct.

Form of Detergent Compositions

When the compositions of the invention are detergent compositions, the compositions can have any suitable form, for example granules, tablets, pouches, syndet bars, gels, pastes or the like. Other suitable forms include heavy-duty liquid laundry detergents, substantially nonaqueous laundry detergents in liquid or solid form, and aqueous forms of any of said detergents.

Advantages

The present invention has numerous advantages. For example, it can be used to deliver hydrophobic photobleaches to soiled fabrics. It is useful in nonaqueous cleaning, e.g., dry-cleaning. The invention. permits dispersing the photobleach into other materials with very low energy requirements and without organic solvents, and completely avoids the problems of dispersing crystalline photobleaches in other materials. The invention provides improved photobleaching of dingy soils. The invention accommodates a range of hydrophobic photobleaches, providing flexibility to the formulator. In short, the invention is a significant technical advance.

Other Embodiments

While the present photobleach compounds are. especially directed to use in consumer product compositions, especially for photobleaching detergents, the present compounds are useful for other purposes, for example as dyes, hueing agents, photodisinfectants and the like. The present invention includes all such benefits of the compounds, and all consumer product compositions containing same.

Moreover it is believed that the present compositions may also be useful in any other context or product in which a hydrophobic nonionic photoactive compound is required. Such applications include photodynamic therapy and the electronics industry.

EXAMPLES

Example I-1

Preparation of a Hydrophobic Liquid Photobleach

A photobleach compound having the following formula is prepared:

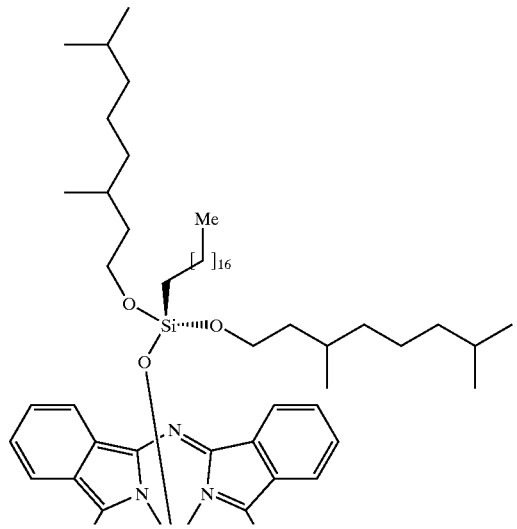

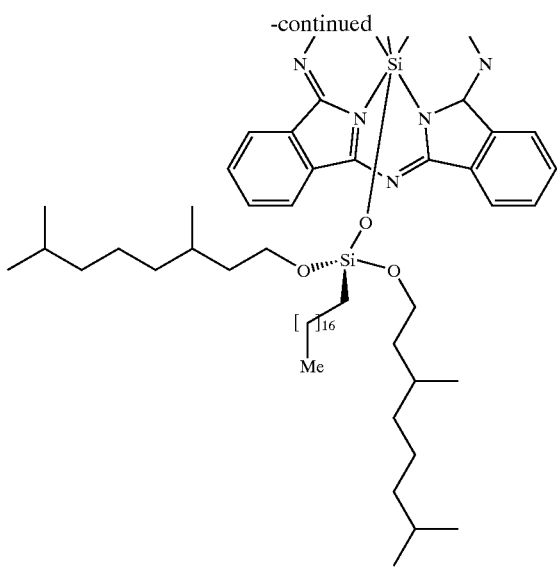

SiPc[OSi((CH$_2$)$_{17}$CH$_3$)(O(CH$_2$)$_2$CH(CH$_3$) (CH$_2$)$_3$CH(CH$_3$)$_2$)$_2$]$_2$ Under Ar atmosphere a solution of (CH$_3$O)SiCl$_2$(CH$_2$)$_{17}$CH$_3$ (0.3 mL, 0.72 mmol) and a solution of (CH$_3$)$_2$CH(CH$_2$)$_3$CH(CH$_3$)CH$_2$CH$_2$OH (0.4 mL, 2.123 mmol) and toluene (15 mL) dried by distillation (~5 mL of distillate) is refluxed for 0.5 h. The resulting solution is added to a suspension of SiPc(OH)$_2$ (160 mg, 0.280 mmol) and pyridine (50 mL) dried by distillation (~5 mL of distillate), and the mixture formed is slowly distilled for 3 h (~20 mL of distillate), concentrated by rotary evaporation (~10 Torr, ~40° C.). The concentration is diluted with hexanes (20 mL), the suspension formed is filtered and the filtrate is concentrated by rotary evaporation (~60 Torr, ~30° C.). The concentrate is chromatographed (hexanes, Al$_2$O$_3$ III, hexanes-toluene, 4:1), further chromatographed (hexanes, Silicagel hexanes-CH$_2$Cl$_2$, 4:1), and evaporated to dryness with a rotary evaporator (~10 Torr, ~40° C.), dried and weighed (96 mg, 0.054 mmol, 19% yield based on SiPc(OH)$_2$). Mp<25° C. UV-vis ($\lambda$max$^{(nm)}$; hexanes) 666. NMR (300 MHz, CDCl$_3$): $\delta$9.85 (m, 1.4-ArH), 8.27 (m, 2,3-ArH), 1.40 (m, SiR$_{od}$-17CH$_2$), 1.30 (m, SiR$_{od}$-7-16 CH$_2$, $_{SiORdo}$-6CH$_2$; SiOR$_{do}$-7 CH), 1.19 (m, SiR$_{od}$-6 CH$_2$), 1.00 (m, SiOR$_{do}$-5 CH$_2$), 0.98 (t, SiR$_{od}$ CH$_3$), 0.89 (d, SiOR$_{do}$-8 CH$_3$), 0.80 (m, SiR$_{od}$-4 CH$_2$), 0.22 (m, SiOR$_{do}$-3 CCH$_3$), –0.05 (m, SiOR$_{do}$-1 CH$_2$), –0.17 (m, SiR$_{od}$-3 CH$_2$), –1.23 (m, SiR$_{od}$-2 CH$_2$), –2.32 (m, SiR$_{od}$-1 CH$_2$). The compound is a blue-oil and is photoactive.

Consumer Product Composition Examples

Example 2

Dry-Cleaning Additive

The compound of Example 1 at a concentration of 500 ppm is mixed with PEG 4,000. The mixture permits more convenient handling of the photobleach. The mixture is used as a dry-cleaning additive in a conventional dry-cleaning operation. Photobleaching occurs when the dry-cleaned fabrics are worn.

Example 3

Dry-Cleaning Additive

The compound of Example 1 at a concentration of 500 ppm is mixed with PEG 4,000. The mixture permits more convenient handling of the photobleach. The mixture is used as a dry-cleaning additive in a dry-cleaning operation. The dry-cleaning operation is modified by the inclusion of a light source. Photobleaching occurs in the dry-cleaning appliance.

Example 4

Pre-Treater

The compound of Example 1 at a concentration of 500 ppm is mixed with stearic acid and formed into a stick. The stick permits direct application of the photobleach to a stained fabric. The mixture is used as a dry-cleaning pretreat additive or directly by the consumer, especially immediately after staining a fabric. For example, the stick is directly applied to a curry stain on a tablecloth. In this manner, the curry stain is treated a good while before it can be sent for laundering. Photobleaching occurs when the fabric is exposed to light.

Example 5

Spray Treater

The compound of Example 1 at a concentration of 500 ppm is mixed with a fluorocarbon solvent and placed in a spray bottle or aerosol can. The spray application permits treatment of a surface having a more extended area than that of a localized stain. Photobleaching occurs when the treated surface is exposed to light.

Example 6

Laundry Detergent Compositions Having Granular Form

| Ingredients | weight % | | | |
|---|---|---|---|---|
| | 6-1 | 6-2 | 6-3 | 6-4 |
| Photobleach of Example 1 | 0.01 | 0.10 | 0.20 | 0.30 |
| Detersive surfactant | 15 | 30 | 20 | 25 |
| Sodium C$_{11}$ Linear Alkylbenzene | | | | |

-continued

Laundry Detergent Compositions Having Granular Form

| Ingredients | weight % | | | |
|---|---|---|---|---|
| | 6-1 | 6-2 | 6-3 | 6-4 |
| Sulfonate Detersive surfactant | 0 | 1 | 1 | 1 |
| $C_{24}E_5$ or $C_{45}E_{5-7}$ nonionic Detersive surfactant | 0.5 | 1 | 0.5 | 0 |
| $C_{12}$ alkyldimethylammonium chloride Builder | 15 | 35 | 22 | 0 |
| Sodium Tripolyphosphate Builder | 0 | 0 | 0 | 30 |
| Zeolite Na A (1–10 micron) Builder | 10 | 10 | 15 | 15 |
| Sodium Carbonate Anhydrous Dispersant | 2 | 2 | 0 | 2 |
| Sokalan ® CP5 (BASF) Antiredeposition agent | 0 | 0.1 | 1 | 1 |
| Carboxymethyl Cellulose Brightener | 0.1 | 0 | 0 | 0 |
| Tinopal ® CBS-X (CIBA) Brightener Mixture (CIBA) | 0 | 0.1 | 0.1 | 0 |
| Soil Release Agent[1] | 0.2 | 0.2 | 0 | 0.3 |
| Enzyme Savinase ® 6.0T (Novo) | 0 | 0.6 | 0.5 | 0.6 |
| Enzyme BAN ® 300T (Novo) | 0 | 0.1 | 0.5 | 0.6 |
| Enzyme Lipolase ® 100T (Novo) | 0 | 0 | 0.2 | 0.3 |
| Enzyme Carezyme ® 5T (Novo) | 0 | 0.2 | 0.2 | 0.3 |
| Bleach Sodium Perborate Monohydrate | 0 | 0 | 3.0 | 5.0 |
| Bleach Activator Nonanoyloxybenzene sulfonate, Na salt | 0 | 0 | 2.0 | 3.0 |
| Moisture + Sodium Sulfate + Perfume + Miscellaneous | Balance to 100 | Balance to 100 | Balance to 100 | Balance to 100 |

[1]. Soil Release Agent according to U.S. Pat. No. 5,415,807 Gosselink et al., issued May 16, 1995.

Example 7

Fabric Softener

The compound of Example 1 at a concentration of 500 ppm is mixed with a commercial fabric softener sold as DOWNY® by the Procter & Gamble Co. The softener is used in the normal manner. Photobleaching occurs when the treated fabrics are exposed to light.

What is claimed is:

1. A compound having the formula:

$$Si(IV)(Pc)L_2$$

wherein PC is phthalocyanine and L represents said axial ligands; and wherein each L can vary independently and is selected from the group consisting of:

$$—Osi(R^1)(OR^2)_2$$

wherein $R^1$ is a hydrocarbyl moiety having 12 or more carbon atoms and $R^2$ is a branched hydrocarbyl moiety having 10 or more carbon atoms.

2. A composition comprising at least about 0.001 ppm of a compound according to claim 1.

3. A method of cleaning a fabric comprising the step of treating the fabric with a composition comprising a photobleach compound having the formula:

$$Si(IV)(Pc)L_2$$

wherein PC is phthalocyanine and L represents said axial ligands; and wherein each L can vary independently and is selected from the group consisting of:

$$—Osi(R^1)(OR^2)_2$$

wherein $R^1$ is a hydrocarbyl moiety having 12 or more carbon atoms and $R^2$ is a branched hydrocarbyl moiety having 10 or more carbon atoms.

4. The method of claim 3 wherein the composition comprises at least about 0.001 ppm of the photobleach compound.

5. A method of cleaning dingy fabric comprising the step of treating the dingy fabric with a composition comprising a photobleach compound having the formula:

$$Si(IV)(Pc)L_2$$

wherein PC is phthalocyanine and L represents said axial ligans; and wherein each L can vary independently and is selected from the group consisting of:

$$—Osi(R^1)(OR^2)_2$$

wherein $R^1$ is a hydrocarbyl moiety having 12 or more carbon atoms and $R^2$ is a branched hydrocarbyl moiety having 10 or more carbon atoms.

6. The method of claim 5 wherein the composition comprises at least about 0.001 ppm of the photobleach compound.

7. A composition comprising a compound of claim 1 in combination with a detersive surfactant, solvent, propellant, polymeric carrier, builder, chelant, bleach system, soil release polymer, softener, perfume, dye, or a mixture thereof.

8. The composition of claim 7 wherein the detersive surfactant is an anionic, cationic, zwitterionic, or non-ionic detersive surfactant or a blend thereof.

9. The composition of claim 8 wherein the composition is in the form of granules, powders, tablets, liquids, gels or pastes.

* * * * *